United States Patent
Prisco et al.

(10) Patent No.: US 9,423,049 B2
(45) Date of Patent: *Aug. 23, 2016

(54) READING AND ADJUSTING TOOL FOR HYDROCEPHALUS SHUNT VALVE

(71) Applicant: MEDTRONIC XOMED, INC., Jacksonville, FL (US)

(72) Inventors: John R. Prisco, Jacksonville, FL (US); John Murdock Murphy, Jacksonville, FL (US); Jamie Hei, Jacksonville, FL (US); Laetitia Mayor, La Sarraz (CH); Pierre Jaquier, Avenches (CH)

(73) Assignee: Medtronic Xomed, Inc., Jacksonville, FL (US)

( * ) Notice: Subject to any disclaimer, the term of this patent is extended or adjusted under 35 U.S.C. 154(b) by 24 days.

This patent is subject to a terminal disclaimer.

(21) Appl. No.: 14/467,587

(22) Filed: Aug. 25, 2014

(65) Prior Publication Data

US 2014/0360598 A1 Dec. 11, 2014

Related U.S. Application Data

(63) Continuation of application No. 13/015,195, filed on Jan. 27, 2011, now Pat. No. 8,813,757.

(51) Int. Cl.
*A61M 27/00* (2006.01)
*F16K 37/00* (2006.01)

(52) U.S. Cl.
CPC ........ *F16K 37/0041* (2013.01); *A61M 27/006* (2013.01); *Y10T 137/7761* (2015.04); *Y10T 137/8242* (2015.04)

(58) Field of Classification Search
CPC .................................................. A61M 27/006
See application file for complete search history.

(56) References Cited

U.S. PATENT DOCUMENTS

| 4,026,276 A | 5/1977 | Chubbuck |
| 4,361,153 A | 11/1982 | Slocum et al. |
| 4,595,390 A | 6/1986 | Hakim et al. |
| 4,615,691 A | 10/1986 | Hakim et al. |

(Continued)

FOREIGN PATENT DOCUMENTS

| EP | 0421557 | 4/1991 |
| EP | 0735662 | 11/1999 |

(Continued)

OTHER PUBLICATIONS

PCT Search Report mailed Jun. 4, 2012, 12 pgs.

*Primary Examiner* — Eric Keasel
(74) *Attorney, Agent, or Firm* — Dicke, Billig & Czaja, PLLC

(57) ABSTRACT

A reading and adjustment tool for use with a valve having a pressure or flow setting adjustable to a plurality of pressure or flow settings is disclosed. The tool includes a signal generator and an excitation coil coupled to the signal generator. The signal generator includes an adjustment interface configured to generate an adjustment signal to adjust the pressure or flow setting and a reading interface to generate a reading signal to read the pressure or flow setting of the valve. At least one excitation coil is connected to the signal generator and configured to generate an oscillating electromagnetic field based on one of the adjustment signal and reading signal. A sense coil can include two portions positioned on either side of the at least one excitation coil to determine the pressure or flow setting of the valve.

11 Claims, 4 Drawing Sheets

(56) References Cited

U.S. PATENT DOCUMENTS

| | | |
|---|---|---|
| 5,425,382 A | 6/1995 | Golden et al. |
| 5,637,083 A | 6/1997 | Bertrand et al. |
| 5,704,352 A * | 1/1998 | Tremblay ............. A61B 5/0031 |
| | | 600/300 |
| 5,879,297 A | 3/1999 | Haynor et al. |
| 6,129,668 A | 10/2000 | Haynor et al. |
| 6,206,835 B1 * | 3/2001 | Spillman, Jr. .......... A61B 5/076 |
| | | 128/903 |
| 6,216,028 B1 | 4/2001 | Haynor et al. |
| 6,326,760 B1 | 12/2001 | Cardoletti et al. |
| 6,485,449 B2 | 11/2002 | Ito |
| 7,245,117 B1 * | 7/2007 | Joy ....................... G01D 21/00 |
| | | 324/601 |
| 7,334,582 B2 | 2/2008 | Bertrand et al. |
| 7,443,128 B2 | 10/2008 | Bieler et al. |
| 7,842,004 B2 * | 11/2010 | Kassem ............. A61M 27/006 |
| | | 604/9 |
| 8,241,240 B2 | 8/2012 | Murphy |
| 8,298,168 B2 | 10/2012 | Bertrand et al. |
| 8,813,757 B2 * | 8/2014 | Prisco ................. A61M 27/006 |
| | | 128/899 |
| 2002/0022793 A1 | 2/2002 | Bertrand et al. |
| 2006/0186846 A1 | 8/2006 | Lassen |
| 2008/0221436 A1 | 9/2008 | Bertrand et al. |
| 2009/0112147 A1 * | 4/2009 | Kassem ............. A61M 27/006 |
| | | 604/9 |
| 2009/0204019 A1 | 8/2009 | Ginggen et al. |

FOREIGN PATENT DOCUMENTS

| | | |
|---|---|---|
| EP | 1512428 | 9/2005 |
| EP | 2090330 | 8/2009 |
| JP | 6040063 | 3/1985 |
| WO | 0054826 | 9/2000 |
| WO | 2009077811 | 6/2009 |
| WO | 2011056743 | 5/2011 |

* cited by examiner

ND ADJUSTING TOOL FOR
READING AND ADJUSTING TOOL FOR HYDROCEPHALUS SHUNT VALVE

CROSS REFERENCE TO RELATED APPLICATIONS

This application is a continuation of U.S. application Ser. No. 13/015,195, now U.S. Pat. No. 8,813,757, filed on Jan. 27, 2011, hereby incorporated by reference in its entirety.

BACKGROUND

1. Technical Field

This disclosure relates generally to surgically implanted physiological shunt systems and related flow control devices. More particularly, the present disclosure relates to a position indicator and adjustment tool for such shunt systems having variable pressure or flow settings for the one-way flow control valves controlling the flow of Cerebral Spinal Fluid (CSF) out of a brain ventricle and preventing backflow of fluid into the brain ventricle.

2. Description of Related Art

A typical adult has a total of about 120-150 cubic centimeters (cc) of CSF with about 40 cc in ventricles in the brain. A typical adult also produces about 400-500 cc/day of CSF, all of which is reabsorbed into the blood stream on a continuous basis.

Sometimes, the brain produces excess CSF or there can be a blockage of the normal CSF pathways and or absorption sites resulting in a condition known as hydrocephalus. Hydrocephalus is a condition of excessive accumulation of CSF in the ventricles or brain tissue. Hydrocephalus can result from genetic conditions, from trauma to the brain or as a person ages.

Excessive accumulation of CSF, due to hydrocephalus or other causes, manifests itself as increased pressure within the brain. Whatever the cause, over time, this increased CSF pressure causes damage to the brain tissue. It has been found that relieving the CSF pressure is therapeutically beneficial. This relief is usually performed by draining CSF from the ventricles.

Patients with hydrocephalus normally require, at least over some time period, continuous drainage of excess CSF to maintain normal CSF pressure in the brain. Excessive CSF accumulated in the ventricles of the brain is typically drained away from the brain using a shunt system.

Where hydrocephalus is a chronic condition, the shunt system typically drains the CSF into the patient's peritoneal cavity or into the patient's vascular system. Such shunt systems typically have a catheter implanted in the ventricle of the brain. The catheter is connected to a fluid control device which is in turn connected to a catheter which empties in to the patient's peritoneal cavity or into the patient's vascular system. An example of a fluid control device is shown in U.S. Pat. No. 5,637,083 issued to William J. Bertrand and David A. Watson on Jun. 10, 1997 entitled "Implantable Adjustable Fluid Flow Control Valve", the teaching of which is incorporated herein in its entirety by reference. Current fluid control devices include an inlet connector, an outlet connector and a valve positioned between the inlet connector and the outlet connector. The valve includes a mechanism to control fluid flow through the valve. In some instances, the mechanism includes a magnet embedded within the valve. Rotating a rotor or otherwise shifting of the rotor position changes the internal configuration of the mechanism. Changing the internal configuration of the mechanism produces a variety of pressure or flow characteristics for the valve. As the internal configuration of the valve changes, the pressure or flow characteristics of the valve change.

In use, the valve is subcutaneously placed on the patient's skull. The catheter going to the patient's ventricle is attached to the inlet connector. The catheter going to the patient's peritoneal cavity or vascular system is attached to the outlet connector. In this way, a direction of flow is established from the inlet connector through the valve to the outlet connector. Changing the internal configuration of the mechanism by coupling the external magnet to the internal magnet and rotating the external magnet effects a movement internal to the shunt and produces a variety of pressure or flow characteristics through the valve.

It is desirable to have a number of different settings in order to achieve different pressure and/or flow characteristics of the valve. One complication with current adjustable valves is that once implanted, it is difficult to determine the setting of the valve and/or adjust the setting of the valve. Having more settings for the valve only makes determining and/or adjusting the valve setting more difficult. With some adjustable valves, x-ray images are used to determine the current state or post adjustment state of the valve. By requiring an x-ray, it is time consuming and costly to determine and adjust the valve setting, as well as not being in the best interest of the patient due to x-ray exposure issues.

Another complication with current adjustable valves is compatibility with magnetic resonance imaging (MRI) procedures. As many current adjustable valves utilize magnets for adjusting and/or determining a valve setting, their function can be disrupted due to interaction of magnetic components in the valve with the applied magnetic field created during the MRI procedure. In particular, the valve setting can be altered to a random, undesirable setting. If the valve setting is not returned to the desired setting after the MRI procedure, this situation can be extremely harmful to a patient. As such, the valve setting needs to be immediately reset to the desired setting upon conclusion of the MRI procedure. In any event, improvement of valves for the treatment of hydrocephalus can provide great benefit.

SUMMARY

Concepts presented herein relate to determining and/or adjusting a pressure or flow setting for an implantable medical device. In one embodiment, a reading and adjustment tool for use with a valve having a pressure or flow setting adjustable to a plurality of pressure or flow settings is disclosed. The tool includes a signal generator and an excitation coil coupled to the signal generator. The signal generator includes an adjustment interface configured to generate an adjustment signal to adjust the pressure or flow setting and a reading interface to generate a reading signal to read the pressure or flow setting of the valve. At least one excitation coil is connected to the signal generator and configured to generate an oscillating electromagnetic field based on one of the adjustment signal and the reading signal.

In another embodiment, a handheld valve reading and adjustment tool for use with a valve having a pressure or flow setting adjustable to a plurality of pressure or flow settings is disclosed. The tool includes a signal generator and an excitation coil coupled to the signal generator. A reading coil includes a first coil portion positioned on a first side of the excitation coil and a second coil portion positioned on an opposite side of the excitation coil than the first portion. The tool further includes a signal detector coupled to the reading coil. The signal generator is configured to send a reading signal to the valve and the reading coil is configured to receive an indication of the pressure or flow setting based on the reading signal.

DETAILED DESCRIPTION

Figure 1:
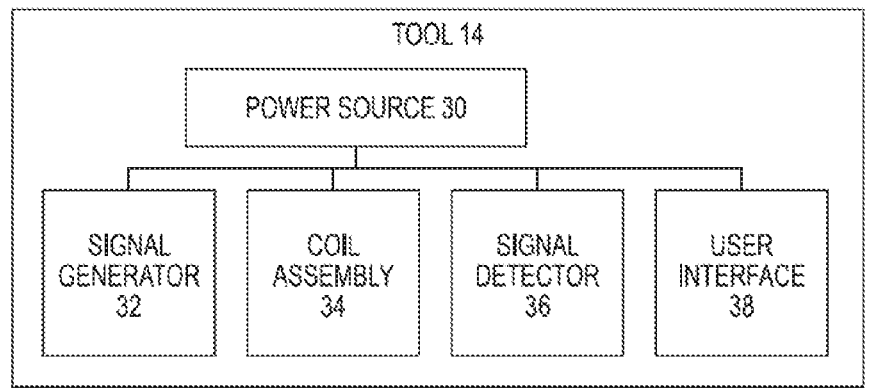
FIG. 1 is a schematic block diagram of an adjustable shunt system.
Figure 1:
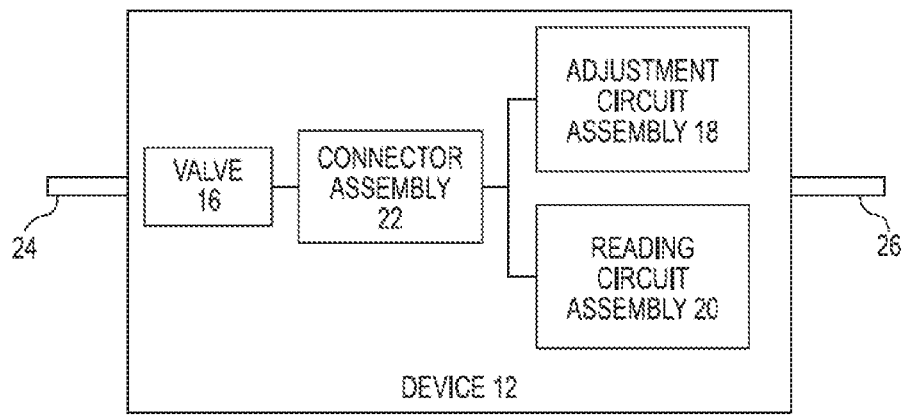

FIG. 1 is a schematic block diagram of an adjustable shunt system 10 including an implantable flow control device 12 (e.g., a shunt) and an electronic valve reader and adjustment tool 14. In general, device 12 can be implanted in a patient to regulate flow of fluids (e.g., CSF discussed above) within the patient based on a pressure or flow setting (also known as a valve setting) for the device 12. Tool 14, in turn, can be a handheld mechanism configured to subcutaneously read and/or adjust the pressure or flow setting of the device 12 when positioned proximate thereto. In particular, the tool 14 can create an oscillating electromagnetic field that is received by device 12. The field can cause device 12 to adjust the pressure or flow setting and/or provide feedback indicative of a pressure or flow setting as will be discussed below.

The device 12 includes a valve 16, an adjustment circuit assembly 18, a reading circuit assembly 20 and a connector assembly 22 coupling the valve 16 with the adjustment circuit assembly 18 and the reading circuit assembly 20. In one embodiment, the adjustment circuit assembly 18 includes an adjustment mechanism that alters a relative position of connector assembly 22 with respect to valve 16, causing a change in the pressure or flow setting of valve 16. Additionally, the connector assembly 22 can include an element that alters a resonant frequency of the reading circuit assembly 20 as a function of the relative position of the connector assembly 22 and valve 16. An exemplary valve is further described in co-pending U.S. patent application Ser. No. 13/015,174 filed on even date herewith, entitled "Adjustment for Hydrocephalus Shunt Valve", the contents of which are hereby incorporated by reference in their entirety. In general, fluid is allowed to flow through the valve 16 from an inlet connector 24 to an outlet connector 26 depending on a valve setting indicative of a cracking pressure (when valve 16 operates as a check valve) for valve 16. The valve 16 defines a number of settings to alter pressure and/or flow characteristics of fluid through device 12. Adjustment circuit assembly 18 is coupled to valve 16 through connector assembly 22 to alter the pressure or flow setting based on signals (e.g., an electromagnetic field) from tool 14. Reading circuit 20 is also coupled to valve 16 through connector assembly 22 and configured to provide a signal indicative of the pressure or flow setting to tool 14 in response to a signal (e.g., an electromagnetic field) from tool 14. Device 12 can be formed of biocompatible materials in order to be subcutaneously positioned within a patient. Additionally, the materials can limit the use of magnetic materials such that a pressure or flow setting for device 12 will not be altered during an MRI procedure.

Tool 14 includes a power source 30 configured to provide power to a signal generator 32, a coil assembly 34, a signal detector 36 and a user interface 38. Signal generator 32 of tool 14 is adapted to provide output signals (e.g., an electromagnetic field) through coil assembly 34 to adjustment circuit assembly 18 and reading circuit assembly 20 within device 12. In particular, the signal generator 32 is coupled to coil assembly 34, which in turn can send output signals that match a resonant frequency of the adjustment circuit assembly 18 and reading circuit assembly 20 in order to induce a current therein. Current induced within the adjustment circuit assembly is used to drive an adjustment mechanism that changes the pressure or flow setting for valve 16. Additionally, current sensed by tool 14 is used to estimate the coupling of the in vivo adjustment circuit assembly 18 with the coil assembly 34. This coupling estimate can be used to guide the user to the valve when setting and to limit the power transmitted to the in vivo adjustment circuit assembly 18. In one embodiment, the adjustment mechanism is a wire formed of shape memory alloy that contracts when current is induced therein, causing the pressure or flow setting to change. In one embodiment, the resonant frequency of adjustment circuit assembly 18 is approximately 100 kHz, although other frequencies can be used.

In a similar manner, signal generator 32 is also adapted to send an output signal (e.g., an electromagnetic field) to reading circuit assembly 20 that matches a resonant frequency of the reading circuit assembly 20. However, the resonant frequency of reading circuit assembly 20 changes as a function of the pressure or flow setting for valve 16. As a result, signal generator 32 is configured to transmit signals for multiple frequencies (e.g., by performing a scanning operation) and determine which frequency is the resonant frequency for reading circuit assembly 20. In particular, when the frequency of the signal handheld is close enough to the valve the signal sent by signal generator 32 induces current within the reading circuit assembly 20, creating a magnetic field that can be sensed by signal detector 36. Based on a strength of the signal detected by signal detector 36, a distance from the tool 14 to the device can be estimated. In one embodiment, the resonant frequency of reading circuit assembly 20 is around 1 MHz (nominally), adjustable within a range of frequencies capable of generation by signal generator 32. Using the resonant frequency information, the pressure or flow setting of valve 16 can be determined, for example using a lookup table.

User interface 38 can provide a visual indication of operation for signal generator 32 and signal detector 36, allow input to the tool 14 and provide a visual indication of proximity of the tool 14 to device 12. For example, user interface 38 can include a screen to display pressure information, one or more buttons to alter operation of tool 14 and/or a set of indicators. The set of indicators, in one embodiment, can indicate a strength of the signal detected by detector 36. If the detected signal is too weak, the user can move the tool 14 closer to device 12 until the tool 14 is in an acceptable working range.

Figure 2:
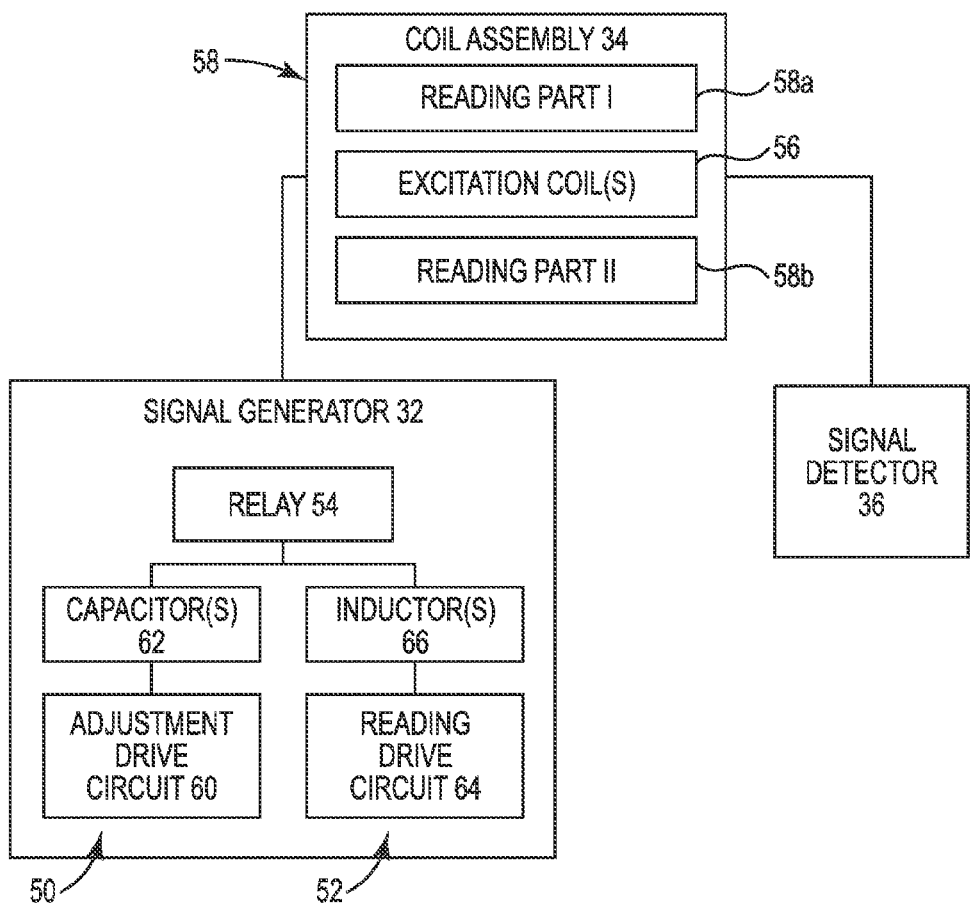
FIG. 2 is a schematic block diagram of a signal generator, coil assembly and signal detector for a handheld tool.

FIG. 2 is a schematic block diagram of select components within tool 14 operable to adjust and/or read a pressure or flow setting of valve 12. FIG. 2 illustrates the signal generator 32, coil assembly 34 and signal detector 36 of FIG. 1. Signal generator 32 includes an adjustment interface 50 and reading interface 52 operably coupled to a relay 54 which is coupled to coil assembly 34. Coil assembly 34 includes an excitation coil 56 and sense (or reading) coil 58 having a first coil portion 58a and a second coil portion 58b positioned on opposite sides of the excitation coil 56. In one embodiment, coil portion 58a and 58b are equally spaced from excitation coil 56. As such, flux from an electromagnetic field generated by excitation coil 56 will be cancelled within coil 58 and thus signal detector 36 will not detect a signal within coil 58. Stated another way, sensing of flux from reading circuit assembly 20 is independent of signals provided by excitation coil 56. In particular, flux passing through coil part 58a will generate a voltage that apposes that generated in coil part 58b, causing cancellation of signals from excitation coil 56 within sense coil 58. If the signal from excitation coil 56 is not cancelled, a calibration process can be performed such that coil 58 does not detect a signal upon generation of a signal within excitation coil 56. Relay 54 is operable to transmit either signals from adjustment interface 50 or reading interface 52 to excitation coil 56, depending on whether tool 14 is in a mode to adjust pressure or flow setting of device 12 or read a pressure or flow setting of device 12. In this manner, relay 54 can select one of an adjustment signal from adjustment interface 50 and a reading signal from reading interface 52 as an output signal delivered to coil 56. In an alternative embodiment, two excitation coils can be utilized, one providing signals from the adjustment interface 50 and one providing signals from the reading interface 52. In this embodiment, relay 54 can be eliminated.

Adjustment interface 50 includes an adjustment drive circuit 60 and one or more capacitors 62. Adjustment drive circuit 60 and capacitors 62 are configured to generate signals that match a resonant frequency of adjustment circuit assembly 18 of FIG. 1. In one example, adjustment drive circuit 60 is embodied as an H-bridge that applies a voltage to the one or more capacitors 62. When device 14 operates in an adjustment mode, relay 54 transmits current from the capacitors 62 to excitation coil 56. In turn, excitation coil 56 creates an oscillating electromagnetic field, based on operation of the adjustment drive circuit 60 and capacitors 62, that is received by device 12 to adjust a pressure or flow setting for the device 12.

Reading interface 52 includes a reading drive circuit 64 inductors 66. Alternatively, inductors 66 can be replaced by capacitors, as desired. In one example, reading drive circuit 64 is embodied as a direct digital sampler configured to scan a number of different frequencies in order to match a particular frequency of reading circuit assembly 20. The reading drive circuit 64 is connected via relay 54 to the excitation coil 56 in coil assembly 34. Current is induced within the reading circuit assembly 20 when the valve is within range of the excitation coil. Current within reading circuit assembly 20 can then be sensed by sense coil 58. In particular, flux created by current in the reading circuit assembly 20 generates a current in coil 58. Detector 36 is coupled to coil 58 so as to determine at what frequency reading circuit assembly 20 is resonant (i.e., by sensing the current induced in reading coil 58 from current generated within the reading circuit assembly 20). The frequency that is determined is indicative of a pressure or flow setting for device 12. This setting can be sent to a user of tool 14, for example via user interface 38.

Figure 3:
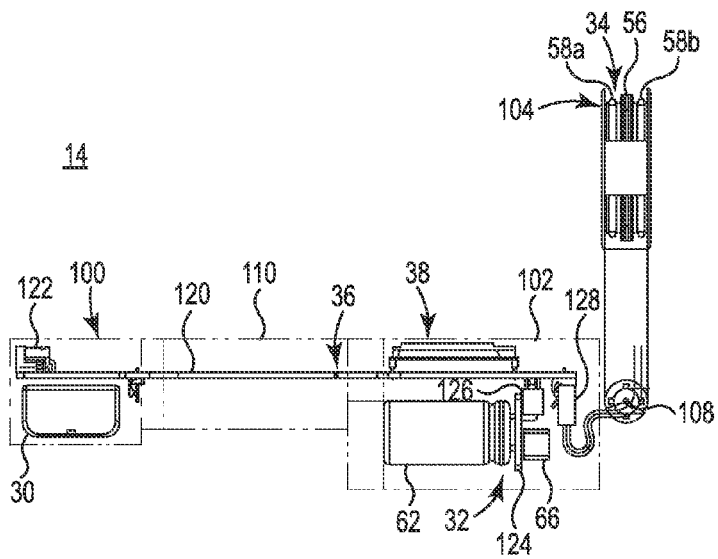
FIG. 3 is a schematic side view of a handheld tool in a first position.
Figure 4:
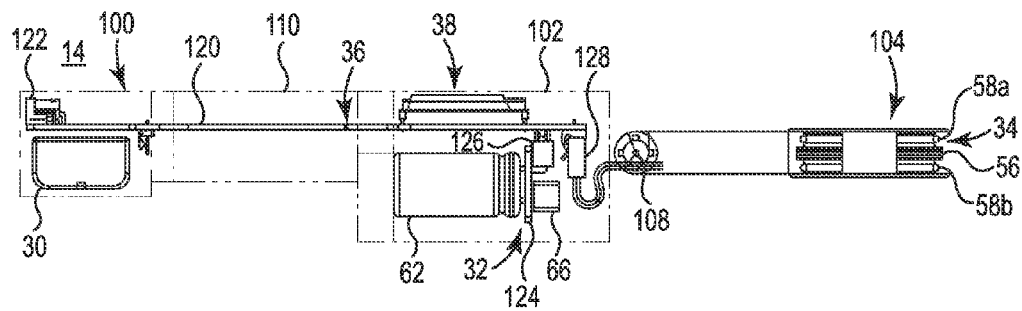
FIG. 4 is a schematic side view of the handheld tool of FIG. 3 in a second position.
Figure 5:
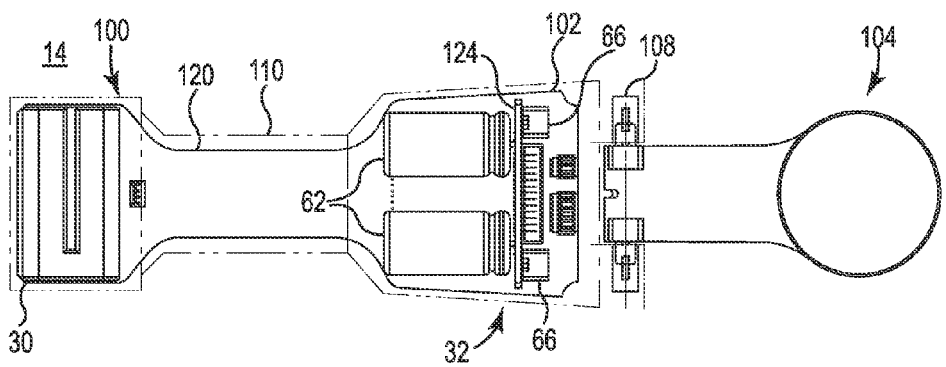
FIG. 5 is a schematic bottom view of the handheld tool of FIG. 4.

FIGS. 3-5 are schematic views of one embodiment of tool 14. Tool 14 includes a housing 100 (referenced generally) that includes a body portion 102 and a coil assembly housing 104 pivotable with respect to body portion 102 about a pivot assembly 108. The coil assembly housing 104 is positionable among a plurality of positions, including a generally perpendicular position with respect to a length of body portion 102 as shown in FIG. 3 and a generally parallel position as shown in FIG. 4. Alternatively, in other embodiments, the coil assembly 104 is movable with respect to the housing 100, for example by tethering with a cord or rotatable about the housing 100. In one embodiment, pivot assembly 108 is a friction hinge that allows selective positioning among a plurality of angles between and including the positions of coil assembly housing 104 in FIGS. 3 and 4. Body portion 102 includes a reduced central portion 110 for convenient grasping by a user. As such, the user is able to easily position tool 14 and, in particular, coil assembly housing 104 proximate the device 12 implanted within a patient.

Components of tool 14 discussed above are positioned within the housing 100. Power source 30, signal generator 32, signal detector 36 and user interface 38 are all positioned within body portion 102, while coil assembly 34 is positioned within coil assembly housing 104. Power source 30, in the embodiment illustrated, is a battery electrically coupled to a main printed circuit board (PCB) 120 positioned within body portion 102. A connector 122 is connectable to an AC to DC external power supply such as a conventional 120 volt alternating current (AC) outlet. Connection of connector 122 to a conventional outlet can recharge battery 30. Signal generator 32 includes a corresponding printed circuit board (PCB) 124 that connects capacitors 62 and inductors 66 to main PCB 120 through a connector 126. Relay 54, adjustment drive circuit 60 and reading drive circuit 64, illustrated in FIG. 2, are not illustrated in FIGS. 3-5, but can be positioned on PCB 120 or PCB 124, as desired. Additionally, circuitry for user interface 38 (referenced generally) can be positioned on PCB 120 and is positioned near a top of body portion 102 so as to be readily viewable by a user. Coil assembly 34 is coupled to PCB 120 through a suitable connector 128.

Figure 6:
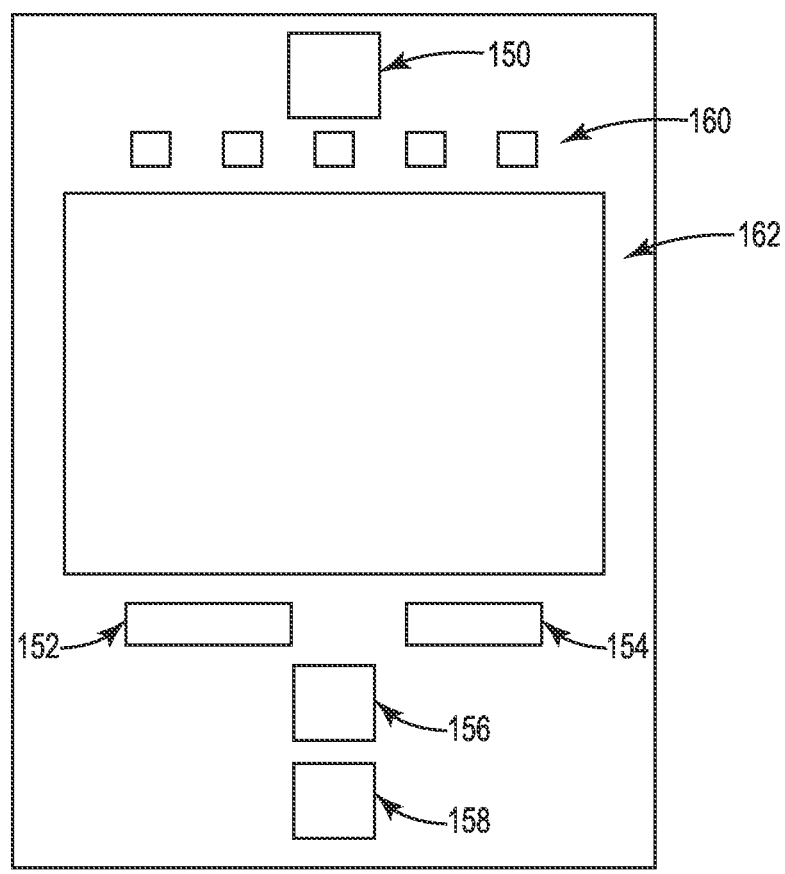
FIG. 6 is a schematic diagram of a user interface for a handheld tool.

Operation of tool 14 is controlled through user interface 38, an example of which is illustrated in FIG. 6. User interface 38 includes a power button 150, a read selection button 152, an adjustment selection button 154 and pressure or flow setting buttons 156 and 158. Power button 150 selectively power on and off tool 14. The read selection button 152 and adjustment selection button 154 are configured to select, respectively, a read mode (to read a pressure or flow setting of device 12) and an adjust mode (to adjust a pressure or flow setting of device 12). Once the adjust mode is selected, pressure or flow setting buttons 156 and 158 can be pressed to adjust the pressure of device 12 up or down, respectively.

User interface 38 further includes a set of indicators 160 (herein illustrated as light emitting diodes) (LEDs)) and a display screen 162 (herein illustrated as a liquid crystal display). The set of indicators 160 can provide indication to a user of proximity between tool 14 and device 12. For example, if all of the indicators are lit, this can be indicative of tool 14 being in close proximity to device 12 such that tool 14 is in a workable range to read and/or adjust a pressure or flow setting of device 12. If none or less than all of the indicators 160 are lit, this can be an indication to the user to move tool 14 closer to device 12. Other ways of providing indications to the user can also be used, such as different colors of LEDs. Screen 162 can be used to display pressure or flow setting information received from device 12 and/or indicate adjustments to the pressure or flow setting that will be made.

Although the present disclosure has been described with reference to preferred embodiments, workers skilled in the art will recognize that changes can be made in form and detail without departing from the spirit and scope of the present disclosure.

What is claimed is:

1. A handheld valve reading and adjustment tool for use with a valve having a pressure or flow setting adjustable to a plurality of pressure or flow settings, comprising:
    a signal generator;
    a coil assembly, comprising:
        an excitation coil coupled to the signal generator; and
        a sense coil, wherein the signal generator is configured to send a reading signal to the valve using the excitation coil and the sense coil is configured to receive an indication signal in response to the reading signal, wherein the signal generator includes an adjustment drive circuit and a reading drive circuit and wherein a relay selects one of the adjustment drive circuit and the reading drive circuit to deliver signals to the excitation coil and the sense coil; and
    a signal detector coupled to the coil assembly to determine a resonant frequency of the indication signal and provide an output signal indicative of the pressure or flow setting based upon the determined resonant frequency.

2. The valve reading and adjustment tool of claim 1, wherein the adjustment drive circuit configured to generate an adjustment signal to adjust the pressure or flow setting of the valve.

3. The valve reading and adjustment instrument tool of claim 2, further comprising at least one capacitor connected with the adjustment drive circuit to generate the adjustment signal.

4. The valve reading and adjustment tool of claim 1, wherein the sense coil includes first and second coil portions equally spaced with respect to the excitation coil.

5. The valve reading and adjustment tool of claim 4, wherein the first coil portion and the second coil portion are positioned and connected in such a way as to cancel a signal from the excitation coil so that the indication signal from the valve can be detected independent of signals generated from the excitation coil.

6. The valve reading and adjustment tool of claim 1 wherein the read drive circuit is configured to generate reading signals of different frequencies to determine the pressure or flow setting of the valve.

7. The valve reading and adjustment tool of claim 6, further comprising at least one inductor connected with the read drive circuit to generate the reading signals.

8. The valve reading and adjustment tool of claim 1, further comprising a user interface providing a display that indicates the pressure or flow setting.

9. The valve reading and adjustment tool of claim 8, wherein the user interface includes a plurality of buttons.

10. The valve reading and adjustment tool of claim 8, wherein the user interface includes at least one indicator to provide an assessment of proximity between the tool and the valve.

11. The valve reading and adjustment tool of claim 1, further comprising a body portion and a coil assembly housing movable with respect to the body portion.

* * * * *